United States Patent [19]

Urban

[11] Patent Number: 4,585,888
[45] Date of Patent: Apr. 29, 1986

[54] SYNTHETIC METHOD FOR A CHIRAL 3-(SUBSTITUTED-PHENYL)-4-(3-HYDROXY-PROPYL)CYCLOHEXANOL

[75] Inventor: Frank J. Urban, Waterford, Conn.

[73] Assignee: Pfizer Inc., New York, N.Y.

[21] Appl. No.: 468,616

[22] Filed: Feb. 22, 1983

[51] Int. Cl.$^4$ .............................................. C07L 69/76
[52] U.S. Cl. ...................................... 560/53; 560/59; 560/126; 560/118; 568/743
[58] Field of Search ............................ 560/126, 53, 59

[56] References Cited

U.S. PATENT DOCUMENTS 4,189,431 2/1980 Johnson ............................... 260/239
4,371,720 2/1983 Johnson et al. ...................... 568/731

OTHER PUBLICATIONS

Otoni, G., *Chem. Pharm. Bull.*, 21(10) 2125–2129, 1973.
Yamada, S., *Tetrahedron Lett.*, (48) 4237–4240, 1969.
Birch, A., *J. Chem. Soc.*, C (2) 125–126, 1967.

*Primary Examiner*—Paul J. Killos
*Attorney, Agent, or Firm*—Charles J. Knuth; Albert E. Frost; Robert K. Blackwood

[57] ABSTRACT

Racemic endo- and exo-1-methoxybicyclo[2.2.2]oct-5-ene-2-carboxylic acids are starting materials for a novel and efficient synthesis of chiral 3R-[2-hydroxy-4-(1,1-dimethylheptyl)phenyl]-4R-(3-hydroxypropyl)-1R-cyclohexanol, a compound having valuable central nervous system (CNS) activity, particularly as an analgesic and as an antiemetic.

14 Claims, No Drawings

SYNTHETIC METHOD FOR A CHIRAL 3-(SUBSTITUTED-PHENYL)-4-(3-HYDROXY-PROPYL)CYCLOHEXANOL

BACKGROUND OF THE INVENTION

The present invention concerns a novel, improved method for the synthesis of 3R-[2-hydroxy-4-(1,1-dimethylheptyl)phenyl]-4R-(3-hydroxypropyl)-1R-cyclohexanol, a chiral compound having valuable central nervous system (CNS) activity, particularly as an analgesic and as an antiemetic. The starting materials for this convenient and efficient synthetic method are racemic endo- and exo-1-methoxybicyclo[2.2.2]oct-5-ene-2-carboxylic acids. The latter compounds are readily synthesized from the corresponding methyl esters, commercially available as a mixture of the endo and exo isomers.

3R-[2-Hydroxy-4-(1,1-dimethylheptyl)phenyl]-4R-(3-hydroxypropyl)-1R-cyclohexanol has been previously described as the highly active levorotatory isomer (enantiomer A) of cis-3-[4-(1,1-dimethylheptyl)-2-hydroxyphenyl]-trans-4-(3-hydroxypropyl)cyclohexanol in Johnson et al., U.S. Pat. No. 4,371,720, which fully discloses how to use that compound, hereinafter referred to as CP-55,940.

Heretofore, CP-55,940 was synthesized from 3-ethoxy-2-cyclohexenone by one or the other of the following routes, where $R^a=$—CH$_2$CH=CH$_2$ or —(CH$_2$)$_3$OCH$_2$C$_6$H$_5$ and $R^b=$

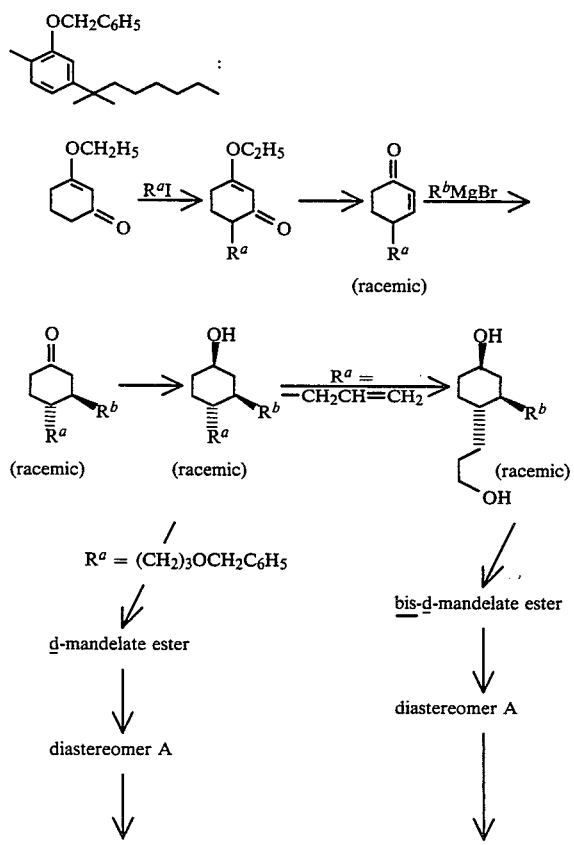

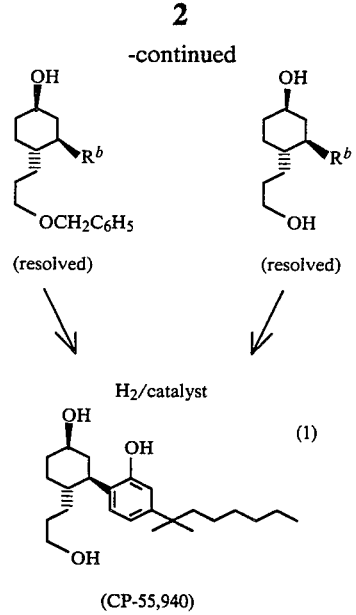

Either synthetic route requires many chemical steps, with resultant low over-all yields. Because resolution to the desired enantiomer occurs very late in the synthesis, these earlier processes are particularly wasteful.

The present invention includes as one step in the process, an unusual rearrangement of a chiral (C$_1$-C$_3$)alkyl 1-hydroxybicyclo[2.2.2]oct-5-en-2-carboxylate to a chiral 4-(2-carbalkoxyethyl)-2-cyclohexenone. Birch et al. have previously described a somewhat related rearrangement of racemic methyl 1-hydroxy-4-methylbicyclo[2.2.2]oct-5-ene-2-carboxylate into 4-(2-carbethoxyethyl)-4-methyl-2-cyclohexenone, J. Chem. Soc. (C), pp. 125–126 (1967).

The present invention also encompasses specific chiral compounds of the formulae (10) and (11) below. These compounds are generally disclosed, without reference to chirality or to their use as intermediates, in the above referenced Johnson et al. U.S. Patent.

SUMMARY OF THE INVENTION

The present invention concerns a process for the preparation of (C$_1$-C$_3$)alkyl S-3-[4-(2-cyclohexenone)]propionate which comprises the sequential steps of:

(a) resolution of racemic (±)-endo- or (±)-exo-1-methoxybicyclo[2.2.2]oct-5-ene-2-carboxylic acid by crystallization of (+)-ephedrine salt of (−)-endo- or (−)-ephedrine salt of (−)-exo-1-methoxybicyclo[2.2.2]oct-5-ene-2-carboxylic acid from a solvent;

(b) aqueous acid treatment of said (+)- or (−)-ephedrine salt to produce (−)-endo- or (−)-exo-1-methoxybicyclo[2.2.2]oct-5-ene-2-carboxylic acid;

(c) esterification of said (−)-endo- or (−)-exocarboxylic acid with a (C$_1$-C$_3$)alkanol to produce (C$_1$-C$_3$)alkyl (−)-endo- or (−)-exo-1-methoxybicyclo[2.2.2]oct-5-ene-2-carboxylate;

(d) demethylation of said (−)-endo- or (−)-exomethoxycarboxylate by the action of boron tribromide to produce (C$_1$-C$_3$)alkyl (+)-endo- or (−)-exo-1-hydroxybicyclo[2.2.2]oct-5-ene-2-carboxylate; and (e) base catalyzed rearrangement of said (+)-endo- or (−)-exohydroxycarboxylate to produce said S-3-[4-(2-cyclohexenone)]propionate.

The present invention further comprises:

(f) reaction of said (C$_1$-C$_3$)alkyl S-3-[4-(2-cyclohexenone)]propionate with a 2-benzyl-4-(1,1-dimethylheptyl)phenyl magnesium halide in the presence of a catalytic amount of a cuprous salt in a reaction inert solvent to produce (C₁-C₃)alkyl 3-[[4R-[3R-((2-benzyloxy-4-(1,1-dimethylheptyl)phenyl))cyclohexanone]]]propionate;

(g) mild hydride reduction of said (C₁-C₃)alkyl 3-[[4R-[3R-((2-benzyloxy-4-(1,1-dimethylheptyl)phenyl))cyclohexanone]]]propionate to (C₁-C₃)alkyl 3-[[4R-[3R-((2-benzyloxy-4-(1,1-dimethylheptyl)phenyl))-1R-cyclohexanol]]]propionate; and (h) strong hydride reduction of said (C₁-C₃)alkyl 3-[[4R-[3R-((2-benzyloxy-4-(1,1-dimethylheptyl)phenyl))-1R-cyclohexanol]]]propionate to produce 3R-[2-benzyloxy-4-(1,1-dimethylheptyl)phenyl]-4R-(3-hydroxypropyl)-1R-cyclohexanol.

The last named compound is a known, chiral intermediate, which is converted to CP-55,940 by known methods (as summarized and referenced above).

As used herein, the expression "reaction-inert solvent" is intended to specify a solvent which does not interact with the starting material(s), reagent(s), intermediate(s) or product(s) of a reaction in a manner which significantly reduces the yield of the desired product(s).

Bicyclo[2.2.2]octene intermediates of the present invention are of the following stereochemical formulae:

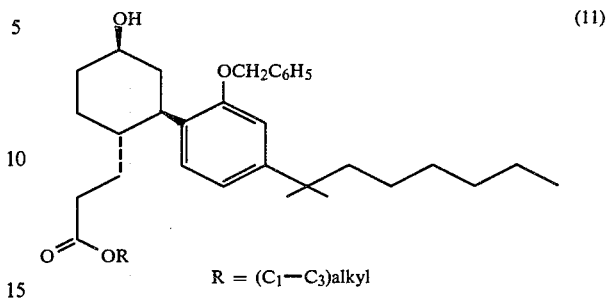

| | endo | | exo |
|---|---|---|---|
| (1) | R = H, R¹ = CH₃; (+)-ephedrine salt | (5) | R = H, R¹ = CH₃; (−)-ephedrine salt |
| (2) | R = H, R¹ = CH₃ | (6) | R = H, R¹ = CH₃ |
| (3) | R = (C₁-C₃)alkyl, R¹ = CH₃ | (7) | R = (C₁-C₃)alkyl, R¹ = CH₃ |
| (4) | R = (C₁-C₃)alkyl, R¹ = H | (8) | R = (C₁-C₃)alkyl, R¹ = H |

Further valuable intermediates of the present invention are of the stereochemical formulae

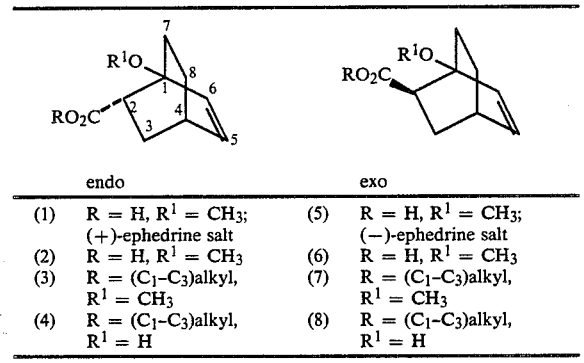

(9)

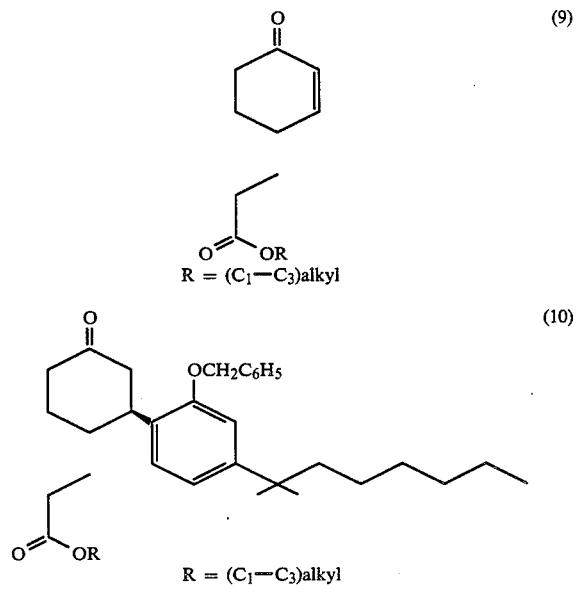

(10)

R = (C₁—C₃)alkyl and (11)

R = (C₁—C₃)alkyl

In the above summarized processes and intermediates, the preferred (C₁-C₃)alkyl group is ethyl.

DETAILED DESCRIPTION OF THE INVENTION

The purified racemic endo- and exo-1-methoxybicyclo[2.2.2]oct-5-ene-2-carboxylic acids required as starting materials for the process of the present invention are readily prepared from commercially available mixed exo/endo isomers of methyl 1-methoxybicyclo[2.2.2]oct-5-ene-2-carboxylate. Exemplary methods are detailed below under Preparations 1-3.

Step (a), resolution of (±)-endo- or (±)-exo-1-methoxybicyclo[2.2.2]oct-5-ene-2-carboxylic acid with (+)-ephedrine or (−)-ephedrine, respectively, is readily carried out by contacting substantially one equivalent each of the appropriate carboxylic acid and ephedrine in a solvent which will separately dissolve at least a portion of the acid and the ephedrine (with warming if necessary) and which will crystallize the desired diastereomeric (+)-ephedrine salt of the (−)-endo acid or the (−)-ephedrine salt of the (−)-exo acid respectively, while leaving the undesired diastereomeric salt in solution. Although other suitable solvents may be identified by experimentation, ethyl acetate has been found to be a solvent particularly well suited for the present purpose. In either case the racemic acid and the chiral ephedrine are preferably combined in warm ethyl acetate (50°-90° C.), conveniently at reflux. The desired diastereomeric salt is recovered by filtration, preferably after cooling to 15°-30° C. and a period of granulation. The desired enantiomeric acid, of the formula (2) or (5) respectively, is recovered in step (b) by standard methods of aqueous acidification (which dissolves the ephedrine, and either precipitates the enantiomeric acid, or forces it into a water immiscible extraction solvent from which it is recovered by evaporation). If desired, the optically active ephedrine base is recovered from mother liquors or raffinates by standard methods, for reuse in the resolution of additional acid.

In step (c), the enantiomeric acid, of the formula (2) or (5), is esterified by standard methods to form a (C₁-C₃)alkyl ester, of the formula (3) or (6), respectively. For example, the acid is taken into excess of the appropriate (C₁-C₃)alkanol in the presence of a strong acid catalyst (e.g., 10-12 mole % of p-toluene-sulfonic acid). Temperature is not critical; while 30°-80° C. is generally suitable, reflux temperature of the (C₁-C₃)alkanol is particularly convenient. Alternatively, esterification is accomplished by activation of the acid as an acid chloride or mixed anhydride, or by use of a dehydrating agent such as dicyclohexylcarbodiimide, or carbonyldiimidazole. The intermediate ester product is recovered by standard methods (e.g., evaporation, extraction, precipitation).

In step (d), the methyl ether group of compounds (3) or (6) is converted to the 1-hydroxy group, forming compounds of the formula (4) or (7), respectively. This conversion is accomplished under anhydrous conditions (thus avoiding ester hydrolysis) by contact with substantially one molar equivalent of a Lewis acid (e.g., $BBr_3$ is particularly well-suited for this purpose), usually in the presence of a reaction-inert solvent (methylene chloride being particularly well-suited) at reduced temperature (e.g., 0° to −60° C., preferably and conveniently −20° to −30° C.). Intermediate product is readily recovered, e.g., by neutralization of acids with excess of a weak base (e.g., aqueous $NaHCO_3$), extraction into a water immiscible organic solvent (e.g., the methylene chloride which may have been used as reaction-inert solvent), and evaporation.

Step (e) converts either the (+)-endo-carboxylate or the (−)-exo-carboxylate, of the formulae (4) and (8) respectively, to the same chiral ($C_1$-$C_3$)alkyl 3-[4-(2-cyclohexenone)]propionate of the formula (9). This unusual rearrangement is readily accomplished in a reaction-inert solvent with a strongly basic catalyst, preferably in t-butanol, in the presence of a catalytic amount of potassium t-butoxide (e.g., 5 mole %) at 0°-50° C., conveniently at ambient temperature. The intermediate product is recovered by standard methods, e.g., by mildly acidic neutralization (e.g., with aqueous pH 6.0 buffer), extraction into an immiscible organic solvent, and evaporation.

To derive the ultimately desired CP-55,940 requires reduction of the ketone group to an alcohol, reduction of the ester group to alcohol, and debenzylation. The reduction of ketone can be accomplished by use of strong hydride reducing agent (also reducing the ester, as described below) or by hydrogenation over a noble metal catalyst (with concurrent debenzylation). In terms of achieving the desired stereospecifity, however, it is preferred to first selectively reduce the carbonyl group with a mild hydride reducing agent, yielding the chiral alcohol ester of the formula (11). The reagent of particular value for this purpose is $NaBH_4$, preferably reacted at reduced temperature (−40° to −75° C.) in a reaction inert solvent which contains a hydroxylic component and a second component which will maintain liquidity of the solvent at the reduced temperature of the reaction. Particularly well suited is a mixture of methanol and tetrahydrofuran (THF).

In the preferred embodiment of the present invention, the chiral alcohol-ester (11) is then reduced to the known CP-55,940 precursor:

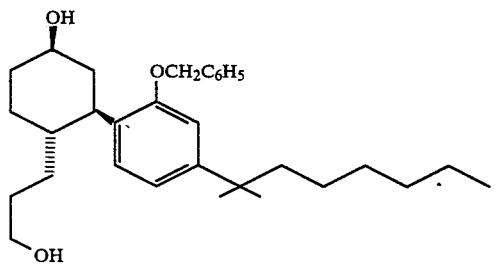

(12)

with a strong hydride reducing agent, in a reaction inert solvent. The preferred reagent for this purpose is $LiAlH_4$ and the preferred solvent is THF. Temperature is not critical, the range 0°-50° C. being preferred.

The known precursor (12) is converted to CP-55,940 by hydrogenation over a noble metal catalyst, according to the known methods referenced and summarized above.

The present invention is illustrated by the following examples. However, it should be understood that the invention is not limited to the specific details of these examples. All temperatures recorded are in degrees Centigrade (°C.).

PREPARATION 1

1-Methoxybicyclo[2.2.2]oct-5-ene-2-carboxylic Acid (Mixed exo/endo Isomers)

In a 3 liter flask equipped with a mechanical stirrer, thermometer, reflux condenser, addition funnel and $N_2$ atmosphere, potassium hydroxide (4.59 mole) was dissolved in methanol (1 L). To the resulting hot solution was added, over a five minute period, methyl 1-methoxybicyclo[2.2.2]oct-5-ene-2-carboxylate (1.53 mole) and the resulting light brown solution was heated to reflux for 5 hours. The reaction was then diluted with $H_2O$ (700 ml) and stripped under reduced pressure to a tan slimy solid. This solid was dissolved in fresh $H_2O$ (1 L) and washed with methylene chloride (1×500 ml). The separated aqueous layer was acidified to pH 1.5 with 420 ml conc. HCl at reduced temperature and extraced with methylene chloride (3×500 ml). The combined organic layers were washed with $H_2O$ (1 L) and brine. Drying and stripping under reduced pressure yielded 87.8% of title product as brown solids; mp 77°-81°; pnmr/$CDCl_3$/TMS/delta 1.65-2.0 (m,6,$C_3H,C_7H,C_8H$), 2.6-2.8 (m,2,$C_4H$, $C_2H$), 3.4 (s, 3,$OCH_3$), 6.2 (m,2,$C_5H,C_6H$).

PREPARATION 2

Iodolactone from 1-Methoxybicyclo[2.2.2]oct-5-ene-2-carboxylic Acid and Recovery of Unreactive Racemic 1-methoxybicyclo[2.2.2]oct-5-ene-2-[exo]carboxylic Acid In a reactor equipped with a mechanical stirrer, thermometer, addition funnel and protected from light, title product of the preceding Preparation (1.32 mole) was dissolved in a mixture of sodium bicarbonate (2.89 mole), $H_2O$ (5 L) and 1N sodium hydroxide (263 ml). The resulting tan solution was then treated with a solution of $H_2O$ (1.5 L), potassium iodide (2.89 mole) and iodine (1.45 mole) yielding a brown suspension which was stirred at ambient temperature for 22 hours. The reaction was then diluted with methylene chloride (1.5 L) and, after stirring for 1.0 hour, was separated and the aqueous phase extracted with fresh methylene chloride. The combined organic extracts were washed with sodium thiosulfate (20% solution, 2×2000 ml), sodium bicarbonate (1×2 L of 20% solution), $H_2O$ (1×1 L). Drying, treating with activated carbon and stripping under reduced pressure gave title iodolactone as an orange solid in 83.15% yield [adjusted for recovered exo-acid below]; mp 125°-126°; ir (KBr) 1781 $cm^{-1}$; pnmr/$CDCl_3$/TMS/delta 4.9 (d,1,$C_6H$), 4.5 (m,1,$C_5H$), 3.25 (s,3,$OCH_3$), 2.9-2.0 (m,7).

The unreacted title exo-acid was isolated by acidifying the basic aqueous layer from the reaction with conc. HCl, extracting with methylene chloride (2×1.5 L) and washing the combined organic layers with sodium thiosulfate (2×2 L of 20% aqueous solution) and H$_2$O (2×2 L). Drying and stripping under reduced pressure yielded a yellow solid accounting for 21.7% of the starting diastereomeric acid mixture; mp 99°–103°; ir (KBr) 1705 cm$^{-1}$; pnmr/CDCl$_3$/TMS/delta 6.3 (m,2, olefinic CH), 3.4 (s,3,OCH$_3$), 2.9–2.4 (m,2,CH), 2.2–1.2 (m,6,CH$_2$).

PREPARATION 3

Racemic 1-Methoxybicyclo[2.2.2]oct-5-ene-2-[endo]carboxylic acid

In a 5 L reactor equipped with reflux condenser, thermometer, mechanical stirrer and N$_2$ atmosphere, a suspension of title iodolactone of the preceding Preparation (0.863 mole) in ethanol (2.5 L) at 22° C. was treated with zinc dust (1.29 mole) added portionwise. The resulting gray suspension was heated at reflux for 3.0 hours and then allowed to cool to room temperature, filtered through a diatomaceous earth pad under N$_2$ cover and the cake washed with fresh ethanol. The yellow filtrate was stripped under reduced pressure to white solids which were partitioned between methylene chloride (1 L) and 2N HCl (1 L). The separated aqueous phase was extracted with fresh methylene chloride (500 ml). The combined organic layers were overlaid with H$_2$O (500 ml), made basic with 15% sodium hydroxide, further diluted with H$_2$O and the layers separated. The latter product rich aqueous layer was washed with methylene chloride (500 ml), acidified (conc. HCl), and extracted with fresh methylene chloride (1×1 L, 2×500 ml). The latter organic layers were combined, back-washed with H$_2$O (500 ml) and brine, dried and stripped under reduced pressure to produce title product as white solids in 94.1% yield; mp 80°–82°; pnmr/CDCl$_3$/TMS/delta 6.2 (m,2,olefinic CH), 3.4 (s,3,OCH$_3$), 2.8 (t,1, $J_{2,3=7\ Hz}$), 2.6 (m,1,C$_4$H), 1.9–1.6 (m,6,CH$_2$).

EXAMPLE 1

(+)-Ephedrine Salt of (−)-1-Methoxybicyclo[2.2.2]oct-5-ene-2-[endo]carboxylic acid (1)

In a reactor equipped with a mechanical stirrer, reflux condenser and addition funnel, the racemic endo acid of the preceding Preparation (0.976 mole) was dissolved in refluxing ethyl acetate (1 L). A solution of (+)-ephedrine (0.976 mole) in warm ethyl acetate (500 ml) was added over a 15 minute period. After refluxing 10 more minutes, the reaction mixture was allowed to cool to ambient temperature, during which solids precipitated. After granulating for 18 hours, crude title product was recovered by filtration, mp 109°. Recrystallization from hot ethyl acetate gave purified title product, 76.8% of theory, mp 129°–130°; [alpha]$_D^{25}$+14.25° (C=1.06, CH$_3$OH); pnmr/CDCl$_3$/TMS/delta 8.1 (s,3,hetero H), 7.2 (m,5,aromatic CH), 6.2 (d,2,olefinic CH), 5.2 (d,1,benzylic CH), 3.3 (s,3, OCH$_3$), 3.1–2.3 (m) and 2.6 (s,N—CH$_3$) 5H total, 2.0–1.3 (m,6,CH$_2$), 1.0 (d,3,CH$_3$).

Analysis: Required: C$_{20}$(69.14%) H$_{29}$(8.41%) N(4.03%). Actual: C(69.25%) H(8.48%) N(4.09%).

EXAMPLE 2

(−)-1-Methoxybicyclo[2.2.2]oct-5-ene-2-[endo]carboxylic Acid (2)

Title free acid was liberated by treating the salt of the preceding Example (0.0288 mole) in methylene chloride (100 ml) with 20% aqueous HCl (50 ml) vigorously stirred for 1.0 hour. The layers were separated and the aqueous extracted with fresh methylene chloride. The combined organic layers were washed with 1N HCl and brine. Drying and stripping under reduced pressure gave title product as a colorless oil which crystallized on standing; 94% yield; mp 57°–60°; ir (KBr) 1704 cm$^{-1}$; [alpha]$_D^{25}$−24.95° (C=1.04,CH$_2$Cl$_2$); pnmr/CDCl$_3$/TMS/delta 6.2 (m,2,olefinic CH), 3.5 (s,3,OCH$_3$), 2.85 (t,1,C$_2$H), 2.6 (m,1,C$_4$H), 2.0–1.5 (m,6,CH$_2$).

EXAMPLE 3

(−) Ethyl 1-Methoxybicyclo[2.2.2]oct-5-ene-2-[endo]carboxylate [(3,R=ethyl)]

In a reactor equipped with reflux condenser and N$_2$ atmosphere, the resolved (−) endo-acid of the preceding Example (0.0247 mole), p-toluenesulfonic acid (2.47 mmole) and ethanol (60 ml) were combined and refluxed for 20 hours. The reaction mixture was stripped under reduced pressure to a yellow oil which was partitioned between H$_2$O and methylene chloride. The separated organic layer was washed with saturated aqueous sodium bicarbonate, 1N HCl and brine. Drying and stripping under reduced pressure gave title product as a light yellow oil in 80% yield; pnmr/CDCl$_3$/TMS/delta 6.1 (m,2,olefinic CH), 4.0 (q,2, J=7 Hz), OCH$_2$CH$_3$), 3.3 (s,3,OCH$_3$), 2.8 (m,1,C$_2$H), 2.5 (m,1,C$_4$H), 2.0–1.4 (m,6,CH$_2$), 1.2 (t,3,J=7 Hz, OCH$_2$CH$_3$); ir (KBr) 1725 cm$^{-1}$; [alpha]$_D^{25}$−6.18°.

EXAMPLE 4

(+) Ethyl 1-Hydroxybicyclo[2.2.2]oct-5-ene-2-[endo]carboxylate [(4), R=ethyl]

Title product of the preceding Example (0.1 mole) was dissolved in methylene chloride (210 ml) and cooled to −30°. By dropwise addition, a methylene chloride solution of boron tribromide (100 ml of 1M) was added over a 15 minute period maintaining a reaction temperature of −30° to −25°. The resulting yellow solution was stirred at −25° to −20° for 1 hour, then carefully poured, under N$_2$ cover, into a mechanically stirred solution of saturated aqueous sodium bicarbonate and wet ice, stirring for 30 minutes. The layers were then separated, the aqueous layer extracted with methylene chloride (200 ml) and combined organic layers washed with H$_2$O and brine. Drying and concentrating in vacuo gave 90.3% of the title product as a yellow oil; [alpha]$_D^{25}$+35.8° (C=1.08, CHCl$_3$); ir (CHCl$_3$) C=O 1709 cm$^{-1}$ —OH 3669 cm$^{-1}$; MS P+ 196; pnmr/CDCl$_3$/TMS/delta 6.05 (d,2,olefinic CH), 4.1 (q over singlet, 3, OCH$_2$CH$_3$ and OH), 2.9–2.4 (m,2,C$_2$H,C$_4$H), 2.2–1.6 (m,6, CH$_2$), 1.2 (t,3,OCH$_2$CH$_3$).

EXAMPLE 5

(−)-Ephedrine Salt of (−)-1-Methoxybicyclo[2.2.2]oct-5-ene-2-[exo]carboxylic Acid (5)

Racemic 1-methoxybicyclo[2.2.2]oct-5-ene-[exo]carboxylic acid (0.302 mole) was dissolved in refluxing ethyl acetate (250 ml) and treated with a solution of (−)-ephedrine (0.302 mole) in warm ethyl acetate (100 ml). The resulting suspension was granulated at room temperature and solids collected by filtration. Redissolving the solids in hot ethyl acetate (750 ml), then cooling and granulating at room temperature gave purified title product, 55.9% of theory; mp 135°–136°; [alpha]$_D^{25}$ −39.55° (C=1.09, CH$_3$OH).

EXAMPLE 6

(−)-1-Methoxybicyclo[2.2.2]oct-5-ene-2-[exo]carboxylic Acid (6)

Title salt of the preceding Example (8 mmole) was stirred with methylene chloride (50 ml) and 20% aqueous HCl (25 ml) for 90 minutes. The phases were separated and the aqueous extracted with fresh methylene chloride. The combined organic layers were washed with 1NHCl, H$_2$O and brine. Drying and concentrating gave title product in 84.9% yield; mp 77°–80°; [alpha]$_D^{25}$ −108.33° (C=1.01, CH$_2$Cl$_2$); pnmr/CDCl$_3$/TMS/delta 6.35 (s,1,C$_6$H), 6.3 (d,1,C$_5$H), 3.5 (s,3,OCH$_3$), 2.8–2.4 (m,2,C$_2$H,C$_4$H), 2.1–1.2 (m,6,CH$_2$).

EXAMPLE 7

(−) Ethyl 1-Methoxybicyclo[2.2.2]oct-5-ene-2-[exo]carboxylate [(7), R=ethyl]

A solution of (−) 1-methoxybicyclo[2.2.2]oct-5-ene-2-[exo]carboxylic acid (5.5 mmole) and p-toluenesulfonic acid (0.66 mole) in ethanol (15 ml) was heated at reflux for 20 hours. The mixture was stripped under reduced pressure to a clear oil which was partitioned between methylene chloride and H$_2$O. The separated aqueous layer was extracted with methylene chloride and the combined organic layers washed with dilute aqueous sodium bicarbonate, 1N HCl and H$_2$O. Drying and concentrating gave title product as a clear oil in 88.3% yield. pnmr/CDCl$_3$/TMS/delta 6.2 (m,2, olefinic CH), 4.0 (q,2,OCH$_2$CH$_3$), 3.3 (s,3,OCH$_3$), 2.8–2.4 (m,2,C$_2$H,C$_4$H), 2.1–1.5 (m,6,CH$_2$), 1.1 (t,3,OCH$_2$CH$_3$).

EXAMPLE 8

(−) Ethyl 1-Hydroxybicyclo[2.2.2]oct-5-ene-2-[exo]carboxylate [(8), R=ethyl]

Title product of the preceding Example (4.8 mmole) in methylene chloride (15 ml) at −25° was treated over a 10 minute period with boron tribromidemethylene chloride solution (1M, 4.8 ml). After 1 hour, the mixture was poured into saturated aqueous sodium bicarbonate and ice, and stirred until foaming subsided. The layers were separated and the aqueous layer extracted with methylene chloride. The combined organic layers were then washed with H$_2$O, dried and concentrated to provide title product as a yellow oil in 75.8% yield; pnmr/CDCl$_3$/TMS/delta 6.1 (m,2, olefinic CH), 4.1 (q,2,J=7 Hz, OCH$_2$CH$_3$), 3.7 (s,1,—OH), 2.6 (m,2, C$_2$H,C$_4$H), 2.2–1.2 (m over t,9,CH$_2$ and OCH$_2$CH$_3$).

EXAMPLE 9

(+) Ethyl 3-[4(2-Cyclohexenone)]propionate [(9), R=ethyl]

Method A

A solution of title product of Example 4 (0.0785 mole) in t-butanol (165 ml) was treated with potassium t-butoxide (3.9 mmole) at ambient temperature. After 45 minutes, the solution was poured into pH 6.0 buffer (150 ml) and ethyl acetate, vigorously stirred for 15 minutes and the layers separated. The aqueous phase was extracted with fresh ethyl acetate and the organic layers combined, back-washed with H$_2$O and brine, dried and concentrated to give title product as a light yellow oil in 92.7% yield; [alpha]$_D^{25}$ +73.84° (C=1.07, CHCl$_3$); pnmr/CDCl$_3$/TMS/delta 6.8 (m,1,C$_3$H), 6.0 (d of d, 1, C$_2$H), 4.1 (q,2,OCH$_2$CH$_3$), 2.6–2.2 (m,5), 2.2–1.5 (m,4), 1.2 (t,3,OCH$_2$CH$_3$). The pH 6.0 buffer was prepared from 4.64 gm KH$_2$PO$_4$, 0.86 gm Na$_2$HPO$_4$, and 200 ml H$_2$O.

Method B

A solution of title product of Example 8 (3.3 mmole) in t-butanol (20 ml) at room temperature was treated with potassium-t-butoxide (0.166 mmole) and stirred for 1 hour. The reaction mixture was then poured into H$_2$O and extracted with ethyl acetate. The separated organic layer was washed with H$_2$O and brine, dried and concentrated to afford title product as a brown oil in 83.9% yield; [alpha]$_D^{25}$ +67.48° (C=1.11, CHCl$_3$); pnmr identical with above Method A product.

EXAMPLE 10

Ethyl 3-[[4R-[3R-((2-benzyloxy-4-(1,1-dimethylheptyl)-phenyl))cyclohexanone]]]propionate (10, R=ethyl)

A solution formed by dissolving 2-benzyloxy-4-(1,1-dimethylheptyl)phenyl bromide (0.377 mole) in tetrahydrofuran (30 ml) was added dropwise to magnesium turnings (0.085 mole) in tetrahydrofuran (30 ml) maintaining a gentle reflux. The Grignard was initiated using a small amount of sodium bis(2-methoxyethoxy)aluminum hydride as catalyst at 65° C. externally heated. When the addition was complete, the mixture was heated at reflux for 90 minutes, then gradually cooled to room temperature, and after 60 minutes, cooled to −20° C. Maintaining that temperature, title product of the preceding Example (0.068 mole) in THF (40 ml) was added dropwise over a 20 minute period with simultaneous addition of cuprous iodide (0.0115 mole) in 3 portions. The resulting yellow mixture was stirred at −20° C. for 45 minutes, then quenched by dropwise addition at 0°–10° C. to an aqueous solution of NH$_4$Cl (3.23 gm/10 ml) forming a thick suspension which, on stirring for 15 minutes in air, gave a tan solid suspended in blue solution. The latter was filtered over diatomaceous earth, with ethyl acetate wash. The combined filtrate and wash was extracted with H$_2$O (50 ml), saturated aqueous ammonium chloride (2×30 ml) and brine, dried and conconcentrated in vacuo to a yellow oil. The oil was chromatographed on silica gel (900 gms) with 10% ethyl acetate-hexane as eluant. The product rich fractions were combined and stripped to yield title product as an oil in 40.24% of theory; [alpha]$_D^{25}$ −20.03° (CHCl$_3$, C=2.521).

EXAMPLE 11

Ethyl 3-[[4R-[3R-((2-benzyloxy-4-(1,1-dimethylheptyl)phenyl))-1R-cyclohexanol]]]propionate (11, R=ethyl)

To a solution formed by combining title product of the preceding Example (0.0175 mole), tetrahydrofuran (40 ml) and methanol (70 ml) at −65° C., there was added (in 4 charges) sodium borohydride (0.02 mole). After stirring for 1.5 hours at −50° C., the reaction was poured into H$_2$O at 0° C. and stripped to about half volume. Extracting with ethyl acetate (1×50 ml, 1×25 ml), washing the combined organic layers with brine, drying and evaporation in vacuo gave a yellow viscous oil. The oil was purified by column chromatography using silica gel support (325 gms) and eluting with 10% ethyl acetate-hexanes, monitoring by TLC (2:1 ether:-hexane). Title product was isolated in 46.5% yield; [alpha]$_D^{25}$ −25.62° [C=1.05, CHCl$_3$]; pnmr/CDCl$_3$/TMS/delta: 7.4 (s,5H); 5.15 (s,2H9; 3.85–4.4 (m,q,4H); 0.8–2.3 (m,29H).

EXAMPLE 12

3R-[2-Benzyloxy-4-(1,1-dimethylheptyl)phenyl]-4R-(3-hydroxypropyl)-1R-cyclohexanol (12)

To a THF solution (35 ml) of title product of the preceding Example (7.4 mmole) at −5° C., lithium aluminum hydride (7.4 mmole) was added portionwise over 10 minutes. The reaction was stirred at 0° for 1 hour; room temperature for 1 hour and reflux for 1.5 hours. Fresh lithium aluminum hydride (3.7 mmole) was added and reflux continued for 1 hour. The reaction, which solidified on cooling to room temperature, was further cooled to 0°–5° C. and diluted with ethyl acetate (30 ml) to form a gray suspension. The latter was carefully added to H$_2$O (30 ml), maintaining pH 5.5 with 1N HCl. The mixture was then filtered through diatomaceous earth. The aqueous layer was separated from the filtrate and extracted with ethyl acetate. The combined organic layers were washed with brine, dried and stripped in vacuo to yield title product as a clear oil, identical with enantiomer A of U.S. Pat. No. 4,371,720, cited above. That same patent document provides specific procedures for converting title product to CP-55,940.

Title product was further characterized by conversion to its bis-d-mandelate ester. Title product (4.9 mmole), d-mandelic acid (10.9 mmole), benzene (35 ml) and p-toluenesulfonic acid (0.1 mmole) were combined and refluxed for 20 hours, collecting the H$_2$O produced in a Dean-Stark trap. The reaction mixture was cooled to room temperature and poured into dilute NaHCO$_3$. The aqueous layer was separated and extracted with ethyl acetate. The combined organic layers were washed with dilute NaHCO$_3$, then H$_2$O, dried and stripped to a tan oil, which was crystallized from isopropyl ether, 38.6% yield; mp 107°–108° C.; [alpha]$_D^{25}$ +30.24° (C=1.035, CHCl$_3$); pnmr/CDCl$_3$/TMS/delta includes 7.3 (2s); 6.8 (m).

I claim:

1. A carbohexacyclic compound having the stereochemical formula

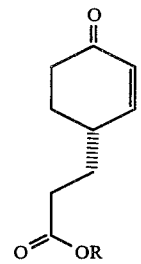
(III)

wherein R is (C$_1$–C$_3$)alkyl.

2. The compound of claim 1 wherein R is ethyl.
3. The compound of claim 2. having the formula (IV).
4. The compound of claim 2. having the formula (V).
5. A carbohexacyclic compound having the stereochemical formula

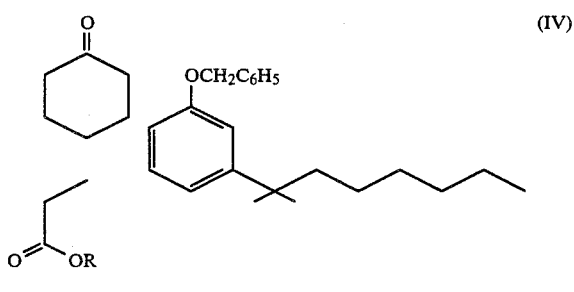
(IV)

or

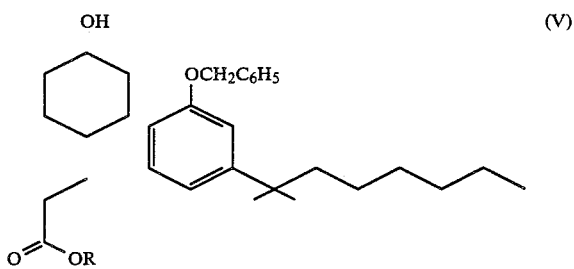
(V)

wherein R is (C$_1$–C$_3$)alkyl.

6. A compound of claim 5 wherein R is ethyl.
7. A process for the preparation of (C$_1$–C$_3$)alkyl S-3-[4-(2-cyclohexenone]propionate which comprises the sequential steps of:
   (a) resolution of racemic (±)-endo- or (±)-exo-1-methoxybicyclo[2.2.2]oct-5-ene-2-carboxylic acid by warming said racemic endo- or exo-compound to 50–90 C. with substantially one molar equivalent of (+)-ephedrine or (−)-ephedrine, respectively, in a solvent; and recovering crystalline (+)-ephedrine salt of (−)-endo- or (−)-ephedrine salt of (−)-exo-1-methoxybicyclo[2.2.2]-oct-5-ene-2-carboxylic acid, respectively;
   (b) aqueous acid treatment of said (+)- or (−)-ephedrine salt to produce (−)-endo- or (−)-exo-1-methoxybicyclo[2.2.2]oct-5-ene-2-carboxylic acid;
   (c) esterification of said (−)-endo- or (−)-exo-carboxylic acid with a (C$_1$–C$_3$)alkanol to produce (C$_1$–C$_3$)alkyl (−)-endo- or (−)-exo-1-methoxybicyclo[2.2.2]oct-5-ene-2-carboxylate;
   (d) demethylation of said (−)-endo- or (−)-exo-methoxycarboxylate by the action of one molar equivalent of boron tribromide in a reaction-inert solvent at 0° to −60° C. to produce (C$_1$–C$_3$)alkyl (+)-endo- or (−)-exo-1-hydroxybicyclo[2.2.2]oct-5-ene-2-carboxylate; and (e) rearrangement of said (+)-endo- or (−)-exohydroxycarboxylate in a reaction inert solvent in the presence of a strongly basic catalyst at 0°–50° C. to produce said S-3-[4-(2-cyclohexenone)]propionate.

8. A process of claim 7 which further comprises reaction of said ($C_1$–$C_3$)alkyl S-3-[4-(2-cyclohexenone)]propionate with a 2-benzyl-4-(1,1-dimethylheptyl)phenylmagnesium halide in the presence of a catalytic amount of a cuprous salt in a reaction inert solvent to produce ($C_1$–$C_3$)alkyl 3-[[4R-[3R-((2-benzyloxy-4-(1,1-dimethylheptyl)phenyl))cyclohexanone]]]propionate.

9. A process of claim 8 which further comprises mild hydride reduction of said ($C_1$–$C_3$)alkyl 3-[[4R-[3R((2-benzyloxy-4-(1,1-dimethylheptyl)phenyl))cyclohexanone]]]propionate to ($C_1$–$C_3$)alkyl 3-[[4R-[3R-((2-benzyloxy-4-(1,1-dimethylheptyl)phenyl))-1R-cyclohexanol]]]propionate.

10. A process of claim 8 which further comprises strong hydride reduction of said ($C_1$–$C_3$)alkyl 3-[[4R-[3R((2-benzyloxy-4-(1,1-dimethylheptyl)phenyl))-1R-cyclohexanol]]]propionate to produce 3R-[2-benzyloxy-4-(1,1-dimethylheptyl)phenyl]-4R-(3-hydroxypropyl)-1R-cyclohexanol.

11. The process of claim 7 wherein the ($C_1$–$C_3$)alkyl group is ethyl.

12. The process of claim 8 wherein the ($C_1$–$C_3$)alkyl group is ethyl.

13. The process of claim 9 wherein the ($C_1$–$C_3$)alkyl group is ethyl.

14. The process of claim 10 wherein the ($C_1$–$C_3$)alkyl group is ethyl.

* * * * *

UNITED STATES PATENT AND TRADEMARK OFFICE
CERTIFICATE OF CORRECTION

PATENT NO.  : 4,585,888
DATED       : April 29, 1986
INVENTOR(S) : Frank J. Urban It is certified that error appears in the above-identified patent and that said Letters Patent is hereby corrected as shown below:

In each of claims 3 and 4, change "2." to -- 6 --.
In claim 5, the formula (IV) should be:

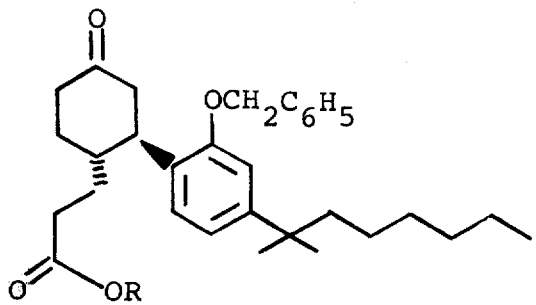

and the formula (V) should be:

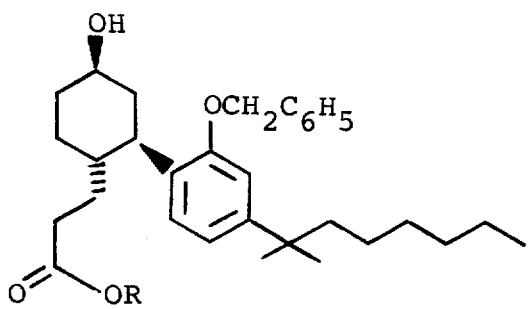

Signed and Sealed this

Twenty-ninth Day of July 1986

[SEAL]

Attest:

DONALD J. QUIGG

Attesting Officer

Commissioner of Patents and Trademarks